(12) United States Patent
Steed

(10) Patent No.: US 7,318,930 B2
(45) Date of Patent: Jan. 15, 2008

(54) CONTROL METHODS FOR BORING BARK BEETLES

(76) Inventor: William Steed, Building C - 109 Braid Street, Westminster, British Columbia (CA) V3L 5H4

(*) Notice: Subject to any disclaimer, the term of this patent is extended or adjusted under 35 U.S.C. 154(b) by 510 days.

(21) Appl. No.: 10/451,385

(22) PCT Filed: Nov. 6, 2002

(86) PCT No.: PCT/CA02/01723

§ 371 (c)(1),
(2), (4) Date: Jun. 23, 2003

(87) PCT Pub. No.: WO03/039253

PCT Pub. Date: May 15, 2003

(65) Prior Publication Data

US 2005/0175655 A1    Aug. 11, 2005

Related U.S. Application Data

(60) Provisional application No. 60/331,134, filed on Nov. 9, 2001.

(51) Int. Cl.
*A01N 25/02* (2006.01)
(52) U.S. Cl. ............... 424/405; 514/731; 514/732; 514/738; 514/557; 514/558; 514/559; 514/560; 514/561; 514/562; 514/563; 514/564; 514/565; 514/566; 514/567; 514/568; 514/569; 514/570; 514/571; 514/572; 514/573; 514/574
(58) Field of Classification Search ............ 514/567, 514/574, 731, 732, 738
See application file for complete search history.

(56) References Cited

U.S. PATENT DOCUMENTS 4,782,094 A * 11/1988 Numata et al. ............ 514/721

FOREIGN PATENT DOCUMENTS

| DE | 3036320 | | 6/1982 |
|---|---|---|---|
| FR | 2228434 | * | 12/1974 |
| JP | 48-18447 | * | 2/1973 |
| JP | 53019650 | * | 2/1978 |
| WO | WO 94/17661 | | 8/1994 |

OTHER PUBLICATIONS

Abstract-1978-52701A WPIX; Insecticide compsn—JP 53019650 Feb. 9, 1978.*
Abstract-1973-33525U WPIX Japanese pine sawyer attractant- JP 48018447 Feb. 3, 1973.*
Chugai Parm Co. Ltd., "Plant growth regulators for accelerating rooting and root growth—contains monophenol(s) e.g. cresol and organic acids, e.g. crotonic acid", *Abstract*, Japan 06 157208 Jun. 3, 1994; Database XP002229020.
Kobayashi, Yukio, "Disinfectants containing acetic acid and pentachlorophenol", *Abstract*, Japan 51 015637 Feb. 7, 1976; Database XP002229019.

* cited by examiner

*Primary Examiner*—Neil S. Levy
(74) *Attorney, Agent, or Firm*—Michael R. Williams; Ryan W. Dupuis; Adrian D. Battison

(57) ABSTRACT

A composition which causes adult boring bark beetles to discontinue boring, discontinue laying eggs and become disoriented and bore out of the tree or cease boring altogether and die is described. Additional tests have shown that beetles will not infest a tree which has been treated with the composition. Furthermore, the composition also causes beetle larvae to cease boring and die and also causes egg sacks to shrivel and die.

11 Claims, No Drawings

CONTROL METHODS FOR BORING BARK BEETLES

PRIOR APPLICATION INFORMATION

This application is a 371 of PCT CA02/01723, filed Nov. 6, 2002 which claims the benefit of U.S. Provisional Application 60/331,134, filed Nov. 9, 2001.

FIELD OF THE INVENTION

The present invention relates generally to the field of insecticides. More specifically, the present invention relates to a method and a composition for treating and/or preventing boring bark beetle infestations.

BACKGROUND OF THE INVENTION

Bark beetles such as the Mountain Pine Beetle—*Dendroctonus ponderosae* Hopkins, Western Pine Beetle—*Dendroctonus brevicomis* LeConte, Spruce Beetle—*Dendroctonus engelmanni* Hopkins, Douglas-fir Beetle—*Dendroctonus pseudotsugae* Hopkins and the Southern Pine Beetle—*Dendroctonus frontalis* Zimmermann, under ideal conditions, can devastate vast areas of forests.

After boring into the target trees, mated adults dig galleries or channels under the bark where eggs are deposited. These eggs hatch into larvae which then feed on the cambium layer beneath the bark, creating channels which cut off the supply of water and nutrients, thereby killing the tree. The larvae then pupate beneath the bark and finally adults emerge from the pupa chamber by boring out through the bark. The disruption of the cambium layer causes the tree to die much as it would if this area was 'ringed' or cut through with an axe or saw.

The beetles carry one or more types fungi on their bodies and, when this fungus germinates within the tree, it spreads and limits the natural uptake of nutrients while turning the wood blue in colour. The damage done by the insects along with the blue stain has the effect of drastically lowering the value of lumber harvested under these conditions. Destruction of conifers, for example, pine, spruce and Douglas fir, by boring bark beetles not only costs the forestry industry, the dead trees also pose a significant fire hazard. Added to the above mentioned costs, additional expenses are involved with replanting damaged areas.

Because the beetles spend the majority of their life cycle protected under the bark of the infested tree, conventional chemical pesticides, applied by traditional methods are of little use.

U.S. Pat. No. 5,281,418 teaches methods and compositions for combating mountain pine beetle (*Dendroctonus ponderosae*) comprising deploying verbenone (4,6,6-trimethylbicyclo[3.1.1]hept-3-en-2-one) from controlled-release devices on or near pine trees. It is of note that it is stated that this compound deters beetle attack on trees but does not disrupt the life cycle of the beetle.

U.S. Pat. No. 4,994,268 teaches the use of pheromones as bait to lure beetles away from specific areas or to keep beetle infestations localized.

U.S. Pat. Nos. 6,051,612 and 6,217,891 teach a method of repelling beetles comprising applying mixtures of bark volatiles from non-infected trees to pine trees in an effort to confuse the beetles and prevent infestation.

Another method of control consists of spraying individual trees with deterrents or insecticides, an expensive and risky solution due to environmental concerns over toxic chemicals. Furthermore, in order to be effective, the insecticide must be able to penetrate the bark of the tree, as discussed above.

Yet another method of control consists of applying monosodium methane arsenate to a continuous shallow cut around the base of a tree. Normal translocation of the compound kills the beetle and its larvae, but the axe cut also kills the tree.

Other methods known in the art for stopping the spread of beetle infestations include sanitation harvesting, wherein infested trees are harvested; fall and burn, wherein infested trees are burned to prevent spreading; and injecting infested trees with pesticide, which is laborious and time-consuming.

As can be seen, the prior art teaches mainly methods of attempting to prevent or contain infestation, not destroying the beetles themselves. As discussed above, other methods require that insecticide be injected into the bark or sections of the bark be removed for application of insecticide, which is time-consuming and potentially damaging to the tree. Thus, the above methods are expensive, labour intensive, and for the most part ineffective. Clearly, an composition for treating and/or preventing boring bark beetle infestations which can be easily and economically applied directly to the barks of trees is needed.

SUMMARY OF THE INVENTION

According to a first aspect of the invention, there is provided a composition for treating and/or preventing boring bark beetle infestation comprising a phenol and a carboxylic acid.

According to a second aspect of the invention, there is provided a method of treating and/or preventing boring bark beetle infestation of a tree comprising providing a composition comprising a phenol and a carboxylic acid; and applying said composition to bark of a tree, thereby preventing bark beetle infestation of said tree and/or treating an existing infestation.

According to a third aspect of the invention, there is provided a method of treating and/or preventing blue-stain fungus infestation of a tree comprising providing a composition comprising a phenol and a carboxylic acid; and applying said composition to bark of a tree, thereby preventing and/or preventing bark beetle infestation of said tree.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "a phenol" refers to compounds of the general formula ArOH, where Ar is phenyl, substituted phenyl, or another aryl group. Examples of phenols include but are by no means limited to carbolic acid, chlorophenol, cresol, hydroxybenzoic acid, catechol, resorcinol, hydroquinone, salicylic acid and the like.

As used herein, "a carboxylic acid" refers to organic acids which contain a carboxyl group, COOH, attached to either an alkyl group or an aryl group. Examples of carboxylic acids include, but are by no means limited to, formic acid, acetic acid, lauric acid, oleic acid, benzoic acid, nitrobenzoic acid, phenylacetic acid and the like.

As used herein, "boring bark beetles" refers to insects which bore into the bark of a tree, for example, but by no means limited to, Mountain pine beetle (*Dendroctonus ponderosae* (Scolytidae)), Spruce beetle (*Dendroctonus rufipennis* (Scolytidae)), Western Pine Beetle (*Dendroctonus brevicomis* (Scolytidae)) and Douglas-fir beetle (*Dendroctonus pseudotsugae* (Scolytidae)).

Typically, boring bark beetles like the pine mountain beetle burrow into the bark of a tree, creating vertical channels with horizontal nodes into which the female lays eggs. Upon hatching, the larvae increase the length of these channels, generally in a horizontal direction, thus cutting the channels which take up moisture and nutrients to the upper portions of the tree. Trees are usually attacked by a number of insect pairs and their efforts can easily ring a tree in a very short time. As discussed above, current methods of control and eradication are extremely labour intensive.

The invention relates to an insecticidal composition for treating and/or preventing boring bark beetle infestation. The composition comprises a mixture of a phenol and a carboxylic acid. When applied to the tree bark, the composition quickly penetrates the bark and enters the cambium which, as discussed above, is where the adult beetles lay their eggs and the beetle larvae develop. In one embodiment, the phenol is carbolic acid and the carboxylic acid is acetic acid, however, as will be appreciated by one knowledgeable in the art, other suitable combinations having similar penetrating and insecticidal properties are within the scope of the invention.

As discussed below, the composition comprises:

10-50% phenol;

5-50% carboxylic acid;

q.v. 100% $H_2O$.

As discussed above, the phenol may be selected from the group consisting of carbolic acid, chlorophenol, cresol, hydroxybenzoic acid, catechol, resorcinol, hydroquinone, salicylic acid and the like. The carboxylic acid may be selected from the group consisting of formic acid, acetic acid, lauric acid, oleic acid, benzoic acid, nitrobenzoic acid, phenylacetic acid and the like.

In some embodiments, the composition further includes a stabilizing agent. In some embodiments, the stabilizing agent is a lower alcohol, although other suitable stabilizing agents known in the art may also be used. In these embodiments, the lower alcohol may be ethanol or methanol. As will be appreciated by one knowledgeable in the art, other suitable alcohols may also be used.

In some embodiments, discussed below, the phenol is carbolic acid and the carboxylic acid is acetic acid. In one embodiment, the composition comprises 5% acetic acid, 10% carbolic acid and 85% water.

Tests have shown that the above-described composition causes adult beetles to discontinue boring, discontinue laying eggs and become disoriented and bore out of the tree or cease boring altogether and die. Furthermore, tests have shown that beetles will not infest a tree which has been treated with the composition. As discussed below, the composition also causes beetle larvae to cease boring and die and also causes egg sacks to shrivel and die.

In some embodiments, the composition also Includes a colouring agent for monitoring application and penetration, as discussed below.

In some embodiments, the composition may be concentrated or otherwise be arranged for subsequent dilution.

In some embodiments, the composition may include propellants or other suitable agents such that the composition can be spray-applied. In other embodiments, the composition may be applied as a gel, paste or embedded in a carrier or applicator using means known in the art.

In use, the composition is applied to trees either infested or at risk of being infested by boring bark beetles. As discussed above, the composition may be sprayed onto the bark of a tree and may include a colouring agent so that penetration of the composition into the tree can be followed. As discussed herein, application of the composition disorients adult beetles and causes them to either exit the tree or stop boring, resulting in their death. Eggs and larvae are also killed by the composition. Thus, the above-described composition acts to prevent or treat boring bark beetle infestation by disrupting the life cycle of the beetle.

EXAMPLE I

Ten sections of pine trees were delivered from Merrit, BC area by the Provincial Forest Service. These sections were approximately 8 feet long and averaged 7 to 10 inches in diameter. The sections had been infested by adult mountain pine beetles approximately one week prior to delivery.

By cutting through the bark in an area above an obvious entry point, a section could be lifted away to reveal a mated pair at work. Removal of the bark for a short period of time did not bother the insects and the pair continued to burrow upwards in the cambium layer. This process was repeated several times with sections of the bark removed at regular intervals to determine the rate at which the insect was burrowing.

The composition was mixed with a colouring agent to facilitate detection of treated areas and rate of passage through the bark. This mixture was then applied to the samples described above.

Initial results indicated that when an area containing active adults was treated by applying the insecticide composition to the outside of the bark directly over the adult insects, the adult insects immediately became disturbed. Specifically, some ceased burrowing while others changed the direction of their channel and still others burrowed completely out of the bark, where they remained. Subsequent examination of the adult beetles that remained in the cambium layer showed that they were either dead or nearly so. Egg laid by the mated adults shrivelled and deteriorated. Hatched larvae and pupae were also killed by the composition.

Similar tests carried out on adult beetles emerging from infested samples showed similar results.

EXAMPLE II

Eight, two meter long sections of lodgepole pine were acquired from the British Columbia Forest Service. These sections ranged from 18 cm to 25 cm in diameter and had recently been infested by pine beetles. At the time the tests began adult beetles had begun to tunnel upwards from their point of entry.

The first group of samples was to be used to test various combinations of compounds on paired adults prior to the laying of eggs. The second group of samples remained undisturbed in order to allow the insects to lay eggs. The third group of samples remained undisturbed in order to allow the eggs to hatch. The fourth group of samples remained undisturbed with the intent of allowing the larvae to enter the pupal stage. Several more sections of the same species were obtained. These had been infested the previous year and were to provide emerging adults for further tests. Unfortunately, the wrapping on these samples was disturbed and the new adults escaped before any serious tests could be accomplished.

The insects in the first sample group were observed by using a sharp instrument to loosen a rectangle of bark to allow it to be temporarily removed from the sample section. After noting the vertical position of the insects in respect to the outside of the sample, the rectangles of bark were replaced and the incisions sealed with tape. Repeated instances of this procedure revealed that the insects continued to tunnel upwards and did not seem to be disturbed by the brief removal of sections of bark.

After locating the active adult pairs, various combinations of the selected compounds were applied to the area surrounding the insects. When the active beetles came in contact with the treated areas, the insect became disturbed and changed the direction of boring. If the compound was applied in a circular or rectangular pattern surrounding the tunnel, the insect seemed reluctant to bore through the treated area and in most cases, became dormant. In a few cases, the insect bored out of the sample. As discussed herein, direct applications of the compounds caused extreme agitation and later death to the adult beetle.

Eggs were located within the undisturbed samples set aside for this purpose by removing sections of bark in the manner described above. Research in other fields has shown that phenol compounds such as carbolic acid will penetrate the eggs of a number of insects to prevent hatching.

Larvae were located within the samples using the bark removal process. Treatment with various mixtures of the selected compounds resulted in almost immediate death of the larvae.

The fourth set of sample sections were set aside to allow the larvae to attain the pupal stage. Treatment of the insect at this point resulted in discolorization; however, as the insect is normally dormant during this period it was difficult to determine the results.

Based on these results, it appears that application of the compounds in such a manner that the insect came in contact with it prior to or during emergence, similar results would occur, thereby protecting the tree from infestation.

FORMULA EXAMPLES

Acetic Acid (ethanoic acid) $CH_3COOH$
Phenol (carbolic acid) $C_6H_5OH$
Ethanol $CH_3CH_2OH$
Methanol $CH_3OH$
Red Dye (Non-reactive—food grade)

As discussed above, a non-reactive colouring agent was added to all solutions in order to exhibit wetting of the outer surface of the bark and coverage on phloem tissue. When penetrating ability and coverage had been defined, the colouring agent was eliminated from the solutions during further tests.
Solution 1: 50% $C_6H_5OH$; 50% $CH_3COOH$
Solution 2: 20% $C_6H_5OH$; 20% $CH_3COOH$; 60% $H_2O$
Solution 3: 10% $C_6H_5OH$; 10% $CH_3COOH$; 80% $H_2O$
Solution 4: 5% $C_6H_5OH$; 5% $CH_3COOH$; 90% $H_2O$
Solution 5: 2% $C_6H_5OH$; 2% $CH_3COOH$; 96% $H_2O$
Solution 6: 10% $C_6H_5OH$; 10% $CH_3COOH$; 10% $CH_3CH_2OH$; 70% $H_2O$
Solution 7: 10% $C_6H_5OH$; 10% $CH_3COOH$; 10% $CH_3OH$; 70% $H_2O$
Solution 8: 5% $C_6H_5OH$; 5% $CH_3COOH$; 5% $CH_3OH$; 85% $H_2O$
Solution 9: 10% $C_6H_5OH$; 5% $CH_3COOH$; 10% $CH_3OH$; 75% $H_2O$
Solution 10: 10% $C_6H_5OH$; 5% $CH_3COOH$; 85% $H_2O$ The above mentioned solutions were judged by penetrating ability and speed as well as for effects on the insect at various stages in its life cycle.

Solution 1 showed rapid penetration; however, this undiluted solution would be expensive and somewhat dangerous to apply. Solutions 2 and 3 showed rapid penetration. Solution 4 showed slow penetration. Solution 5 showed slow, unreliable penetration. Solutions 6 and 7 showed good penetration but no better than Solution 3. Solution 8 showed slow penetration. Solution 9 showed good penetration but no better than in Solution 3. Solution 10 showed rapid penetration and had the added benefit of requiring only minimal volumes of active ingredients.

Effects on the Target Insect:
Solution 1. Violent reaction of adults and larvae, discolorization and deformity of eggs.
Solution 2. Violent reaction of adults and larvae, discolorization and deformity of eggs.
Solution 3. Slower reaction of adults, however larvae and eggs reacted as above.
Solution 4. Unreliable coverage.
Solution 5. Ineffective.
Solution 6. Slower reaction of adults, however larvae and eggs reacted as above.
Solution 7. Slower reaction of adults, however larvae and eggs reacted as above.
Solution 8. Unreliable coverage.
Solution 9. Slower reaction of adults, however larvae and eggs reacted as above.
Solution 10. Violent reaction of adults and larvae, discolorization and deformity of eggs.

SUMMARY

Solutions 1, 2, and 3 penetrated the outer bark well and generally had a lethal effect on adults, eggs and larvae, with solution 3 reacting somewhat more slowly on the adults. Solutions 4 and 5 exhibited very slow penetrating ability and therefore, limited effects on the insect. Solutions 6 and 7 and 9 penetrated well; however, the addition of ethanol and/or methanol did not seem to add to their effectiveness. As discussed above, the addition of ethanol and methanol were intended to provide a more stable composition in the presence of water. Solution 8 reacted much as did solutions 4 and 5. Solution 10 seemed to perform as well as the less diluted solutions both in penetration and effect on the insects.

EXAMPLE IV

Wood Staining Fungi (Blue Staining Fungi):
The relationship between bark beetles and blue-stain fungi is as follows: When the insect infests a tree by boring through the bark and into the phloem tissue, it carries with it the spores of one or more fungi which then infects the sapwood of the inoculated trees. During colonization, female beetles tunnel throughout the phloem tissue of the tree where they lay their eggs. As carriers of *O. minus,* the beetles induce thousands of low dosage fungal inoculations over a large portion of the tree bole allowing the fungus to become well established throughout the phloem before invading the sapwood (xylem). Sapwood occlusion by *O. minus* contributes to the quick death of beetle-attacked trees.

Most sapwood staining fungi are typically blue stain fungi and belong to the genus *Ophiostoma* Syd. & P. Syd. (formerly *Ceratocystis*). Harvey (1979) found that 30 to 65 percent of the stem volume of beetle-killed lodgepole pine (*Pinus contorta* Dougl. ex Loud.) was blue-stained within 9 months. *Ophiostoma clavigerum* is considered by some to be the primary invader of sapwood after beetle infestation and is thought to be the most virulent of the two fungi. The order Ophiostomatales is in the phylum Ascomycota, class Pyrenomycetes (filamentous Ascomycetes). These fungi are often associated with insects, particularly bark beetles that burrow into woody tree tissues where the fungi are competitive saprobes. These fungi are often dispersed on the body, gut, or mycangia (specialized structures on the exoskeleton) of beetles or by mites associated with bark beetles. The fungi may benefit or have an adverse affect on the beetle or mite. In any case, the fungi benefit by being dispersed and introduced into potential host trees. Several of these fungi produce a blue stain in the phloem and xylem of trees, and in some cases are serious plant disease agents (i.e. *O. novoulmi*, the Dutch Elm Disease).

The $C_6H_5OH$ component of the tested compounds is a known anti-fungal compound, also, research indicates that, due to the acidic nature of both compounds involved, the fungal microorganisms mentioned above will be negatively affected by the treatment designed to disrupt the life cycle of the bark beetle.

As discussed above, the above-described composition can be applied to the barks of trees and then rapidly penetrates the bark. Once inside the tree, the composition kills adult beetles or drives them out of the tree. Furthermore, eggs and larvae are also destroyed by the composition. Finally, application of the composition to trees prevents subsequent infestation by the beetles.

Thus, the instant invention is a non-toxic, inexpensive, easy to apply insecticide for treating and/or preventing boring bark beetle infestation.

While the preferred embodiments of the invention have been described above, it will be recognized and understood that various modifications may be made therein, and the appended claims are intended to cover all such modifications which may fall within the spirit and scope of the invention.

The invention claimed is:

1. A method of treating a tree for boring bark beetles comprising
   providing a composition comprising a phenol and a carboxylic acid, said composition comprising:
   10-50% of a phenol;
   5-50% carboxylic acid;
   q.v. 100% $H_2O$; and
   applying said composition to bark of a tree either infested or at risk of being infested by boring bark beetles.

2. The method according to claim 1 wherein the phenol is carbolic acid.

3. The method according to claim 1 wherein the carboxylic acid is acetic acid.

4. The method according to claim 1 wherein the boring bark beetle is selected from the group consisting of: Mountain pine beetle (*Dondroctonus ponderosae* (Scolytidae)), Spruce beetle (*Dendroctonus rufipennis* (Scolytidae)), Western Pine Beetle (*Dendroctonus brevicomis* (Scolytidae)) and Douglas-fir beetle (*Dendroctonus pseudotsugae* (Scolytidae)).

5. The method according to claim 1 wherein the phenol is selected from the group consisting of carbolic acid, chlorophenol, cresol, hydroxybenzoic acid, catechol, resorcinol, hydroquinone and salicylic acid.

6. The method according to claim 1 wherein the carboxylic acid is selected from the group consisting of formic acid, acetic acid, lauric acid, oleic acid, benzoic acid, nitrobenzoic acid and phenylacetic acid.

7. A method of treating a tree for blue-stain fungus infestation comprising
   providing a composition comprising a phenol and a carboxylic acid, said composition comprising:
   10-50% of a phenol;
   5-50% carboxylic acid;
   q.v. 100% $H_2O$; and
   applying said composition to bark of a tree infested by boring bark beetles.

8. The method according to claim 7 wherein the phenol is carbolic acid.

9. The method according to claim 7 wherein the carboxylic acid is acetic acid.

10. The method according to claim 7 wherein the phenol is selected from the group consisting of carbolic acid, chlorophenol, cresol, hydroxybenzoic acid, catechol, resorcinol, hydroquinone and salicylic acid.

11. The method according to claim 7 wherein the carboxylic acid is selected from the group consisting of formic acid, acetic acid, lauric acid, oleic acid, benzoic acid, nitrobenzoic acid and phenylacetic acid.

* * * * *